US012086514B2

(12) United States Patent
Veiga Rivero et al.

(10) Patent No.: US 12,086,514 B2
(45) Date of Patent: Sep. 10, 2024

(54) POST-TRAUMATIC IMMOBILISATION DEVICE AND PRODUCTION METHOD THEREOF

(71) Applicant: XKELET EASYLIFE, S.L., Girona (ES)

(72) Inventors: Ricardo Veiga Rivero, Barcelona (ES); Jordi Tura Ceide, Girona (ES)

(73) Assignee: XKELET EASYLIFE, S.L., Girona (ES)

( * ) Notice: Subject to any disclaimer, the term of this patent is extended or adjusted under 35 U.S.C. 154(b) by 411 days.

(21) Appl. No.: 16/080,956

(22) PCT Filed: Mar. 15, 2017

(86) PCT No.: PCT/ES2017/070144
§ 371 (c)(1),
(2) Date: Aug. 29, 2018

(87) PCT Pub. No.: WO2017/158220
PCT Pub. Date: Sep. 21, 2017

(65) Prior Publication Data
US 2018/0357348 A1 Dec. 13, 2018

(30) Foreign Application Priority Data
Mar. 15, 2016 (ES) .............................. ES201630303

(51) Int. Cl.
*G06F 30/23* (2020.01)
*A61F 5/058* (2006.01)
(Continued)

(52) U.S. Cl.
CPC .............. *G06F 30/23* (2020.01); *A61F 5/058* (2013.01); *A61F 5/05866* (2013.01);
(Continued)

(58) Field of Classification Search
CPC ...... G06F 30/23; G06F 30/00; G06F 2119/18; B33Y 70/00; G16H 10/60; G16H 50/50;
(Continued)

(56) References Cited

U.S. PATENT DOCUMENTS

| 5,836,902 A | * | 11/1998 | Gray | ..................... A61F 5/0111 |
| | | | | 602/5 |
| 2012/0101417 A1 | * | 4/2012 | Joseph | ................ A61F 5/05841 |
| | | | | 602/5 |

(Continued)

OTHER PUBLICATIONS

Kelly, S. et al., "A Review of Wrist Splint Designs for Addictive Manufacture", Dec. 15-16, 2015, Loughborough University Institutional Repository. (Year: 2015).*

Kelly et al.: "A review of wrist splint designs for additive manufacture", IN: Proceedings of 2015 14th Rapid Design, Prototyping and Manufacture conference (RDPM 14), Loughborough, Great Britain (2015).

(Continued)

*Primary Examiner* — Cedric Johnson
(74) *Attorney, Agent, or Firm* — LADAS & PARRY LLP

(57) ABSTRACT

A post-traumatic immobilization device is produced by a method thereof. The device has an architectural form with a rounded shape, formed by at least two complementary rigid parts (1a, 1b), in the form of a mesh (11). The parts define respective concave cavities and include curved connecting ends (12), and fasteners provided with raised portions (13) for the coupling of elastic O-rings (2) that clamp the rigid parts (1a, 1b) to one another. A method produces the post-traumatic immobilization device.

4 Claims, 7 Drawing Sheets

(51) Int. Cl.
*B33Y 70/00* (2020.01)
*G16H 10/60* (2018.01)
*A61F 5/01* (2006.01)
*G06F 119/18* (2020.01)
*G16H 50/50* (2018.01)

(52) U.S. Cl.
CPC .............. *B33Y 70/00* (2014.12); *G16H 10/60* (2018.01); *A61F 5/0104* (2013.01); *A61F 2005/0179* (2013.01); *G06F 2119/18* (2020.01); *G16H 50/50* (2018.01)

(58) Field of Classification Search
CPC .... A61F 5/058; A61F 5/05866; A61F 5/0104; A61F 2005/0179; A61F 5/01
USPC ............................................................ 703/6
See application file for complete search history.

(56) References Cited

U.S. PATENT DOCUMENTS

| | | | |
|---|---|---|---|
| 2013/0030335 A1 | 1/2013 | Norton | |
| 2015/0328016 A1* | 11/2015 | Summit | A61F 5/0123 703/1 |
| 2016/0074203 A1* | 3/2016 | Hall | A61F 5/0585 602/6 |
| 2016/0166420 A1* | 6/2016 | Sheehan | A61F 5/30 602/7 |

OTHER PUBLICATIONS

International Search Reprot for PCT/ES2017/070144, mailed Jul. 26, 2017.
International Search Report for PCT/ES2017/070144, mailed Jul. 26, 2017.

* cited by examiner

POST-TRAUMATIC IMMOBILISATION DEVICE AND PRODUCTION METHOD THEREOF

This application is a National Stage Application of PCT/ES2017/070144, filed 15 Mar. 2017, which claims benefit of application Ser. No. 20/163,0303, filed 15 Mar. 2016 in Spain, which applications are incorporated herein by reference. To the extent appropriate, a claim of priority is made to each of the above-disclosed applications.

OBJECT OF THE INVENTION

The present invention relates to a post-traumatic immobilisation device featuring a structure suited to limiting the displacement of an injured bone or joint. This device, obtained by means of 3D printing, enables an area of the body to be maintained immobile during a set period of time and to maintain the alignment of the bone segments, thus favouring their consolidation.

This invention also includes a procedure for the manufacture of the device in question, and specifically of a protocol for obtaining anthropometric data on the patient in question, and the automatic adaptation of the post-traumatic immobilisation device.

PRIOR ART

Currently, various procedures and materials are used to maintain a part of the body immobilised during a set period of time, and to maintain the alignment of the bone segments; among these, the following are of note:

Gypsum slurry: this corresponds to a technique now abandoned in almost all medical centres. As circumstances or locations might arise which make its use mandatory, it is described herein: equal quantities of powdered orthopaedic plaster and warm water are mixed. Bandages of fine orthopaedic linen are thoroughly soaked in the resulting slurry. The weave of the bandage holds the gypsum slurry. With this bandage, thus soaked in plaster, the binding is performed and the splint is made, as required by the circumstances. The use of hotter water or the addition of alum or common salt accelerates the setting process.

Plastered bandages prepared by the staff: this is also a disappearing procedure, due to economic reasons, convenience and difficulty in its preparation. Thin orthopaedic linen bandages of the desired width are passed through a mass of powdered gypsum. A large quantity of the powdered gypsum is retained in the weave of the lawn, thereby forming the bandage. This must be stored in hermetic containers, to prevent the gypsum, which is a highly hygroscopic substance, from absorbing water from the atmosphere and thus losing its capability to set.

Industrially prepared plaster bandages: these are used almost universally; their quality is guaranteed, their setting time exact, and they are easily stored and handled.

Gypsum for orthopaedic use corresponds chemically to a hydrated calcium sulphate: $CaSO_4 \cdot 2H_2O$.

By means of industrial procedures, it is heated to 120-130°, whereby it loses a water molecule. This causes it to lose the characteristic hardness of limestone, and enables it to be pulverised.

When it retrieves the lost water molecule, either through the addition of water or the absorption thereof from the atmosphere (hygroscopy), it recovers its original hardness.

Thus, the gypsum-treated bandage acquires the hardness required to make immobilisation effective. In this way, a rigid, solid, lightweight, porous bandage at a reasonable price is obtained.

Recently, substitutes for gypsum have appeared, in the form of epoxy resins; on contact with water these acquire hardness and rigidity.

Orthoses, as defined by the ISO, are external supports or other devices applied to the body to modify the functional or structural aspects of the neuromusculoskeletal system.

These may be classified into four groups, according to their function:

Stabilising or immobilising: these maintain a position and prevent undesired movements; they may thus be used in flaccid or spastic paralysis if the aim is to act as a support for a paralysed segment, or to reduce joint amplitude of an inflamed, painful segment. The desired degree of immobilisation varies according to the type of orthosis used. These are the most used in the sphere of AP.

Functional: also termed dynamic, as they incorporate an elastic element to enable the movement of a paralysed limb segment.

Corrective: indicated for the correction of a skeletal deformity. These are most effective if used during childhood development.

Protective: these maintain the alignment of a diseased or injured limb.

They are also classified according to the extremity, joint or anatomical region for which they are intended, as orthoses for:

upper extremity: arm, elbow, hand;
lower extremity: foot-ankle-calf; knee; thigh-hip (splints or harnesses); functional or adaptive for the foot (insoles and orthopaedic footwear).

On the other hand, it should be mentioned that although certain documents are known in the state of the art wherein alternative solutions are disclosed, the applicant has found none which presents technical, structural or constitutive characteristics similar to those presented by the title advocated as claimed herein.

DESCRIPTION OF THE INVENTION

The device which is the object of the invention presents a number of constructive peculiarities intended to immobilise a part of a patient's body for a set period of time and to maintain the alignment of the bone segments affected by a traumatism, favouring their consolidation.

The device is constituted by at least two complementary parts or structures in the form of a mesh, obtained by means of 3D printing, and presenting a design with rounded openings to favour the draining of water in the event of being submerged and its subsequent drying by the air or by the use of a towel or clothing;

The openings defined in the parts or structures in the form of a mesh are also designed to enable access for the dressing of wounds, electro-stimulation treatment and other recovery methods.

Said parts or structures are architecturally executed in a non-porous, biocompatible material, suited to provide the device with torsional and flexural rigidity, and to remain in contact with the skin.

Another of the goals of the invention is to endow said parts with a shape defining a single position for the coupling of the two, and to guarantee their stability in the normal-use position of the device. To this end, the parts or structures feature curved, preferably helicoidal, connecting ends which determine a single coupling position of said parts.

Another goal of the invention is to endow said parts with a suitable means to establish their rapid, simple attachment in a coupled or normal-use position. To this end, these parts or structures feature at their curved connecting ends a number of raised portions for the coupling of a number of elastic O-rings that clamp the rigid parts together, holding them in a normal-use position wherein said parts delimit a housing for the adjusted holding of the part of the body to be immobilised.

It is foreseen that the invention should comprise a number of interchangeable elastic O-rings, of different elastic densities, suited to immobilising the parts of the device in its normal-use position, or to enable a certain separation between said parts, increasing the dimensions of the housing for holding the immobilised limb in an inflammatory process of ischaemic compression (ACS, Acute Compartment Syndrome).

To this end, and in accordance with one embodiment of the invention, it is foreseen that the raised portions for the coupling of the elastic O-rings are delimited by a number of channels defined on the external surface of the parts, said parts being open at their curved connecting ends, and featuring dimensions suited to house the corresponding elastic O-ring in their interior.

Another of the goals of the invention is to endow the aforementioned channels for the coupling of the elastic O-rings with a shape enabling an easily removable coupling or closure, or a coupling which prevents easy access and removal of the O-ring during use of the device.

The housing of the elastic O-ring in the aforementioned channels complicates considerably access to the elastic O-ring, hindering the opening of the device in the absence of a tool suited for the grasping and removal of said elastic O-ring.

In those cases where it is desired that the O-ring should be removable, the parts of the device feature a spherical recess at a peripheral point of the channels forming an area for the grasping and release of the corresponding elastic O-ring.

It should be mentioned that this invention further includes a procedure for the manufacture of the aforementioned device, comprising a protocol for obtaining anthropometric data and the adaptation of post-traumatic immobilisations.

Said procedure comprises:
The obtaining of the patient's data by means of a specific computer application and with standard hardware.
The obtaining of virtual data of the patient's affected limb by means of specific scanning software.
The construction of a virtual device, by means of software which receives instructions via scripts without human intervention, automating the processes for creating the virtual device, and displaying the result in a virtual manner in the computer application.
3D printing of the real device.

DESCRIPTION OF THE FIGURES

As a supplement to the description being made herein, and to aid the better understanding of the characteristics of the invention, a set of drawings is included in the present specification in which, as an illustration but not limited thereby, the following is portrayed.

PREFERRED EMBODIMENT OF THE INVENTION

In the example of an embodiment portrayed in the attached figures, the device is comprised of two rigid parts (1a, 1b), formed from a biocompatible material and presenting an architectural form of a mesh (11), said parts (1a, 1b) defining respective concave cavities which, in a normal-use position of the device, hold the part of the body to be immobilised, as portrayed schematically in figure one.

The device of the invention is designed to enable access to the areas requiring electro-stimulation activity, it being possible to increase the openings of the mesh (11) during the stages of design and processing of the structure without affecting the rigidity, the torsion and the proportion of the device.

The aforementioned parts (1a, 1b) feature curved ends (12), in this case of a helicoidal configuration, determining a single coupled position of the same, and defining a housing for the precise holding of the part of the body to be immobilised.

Figure 3:
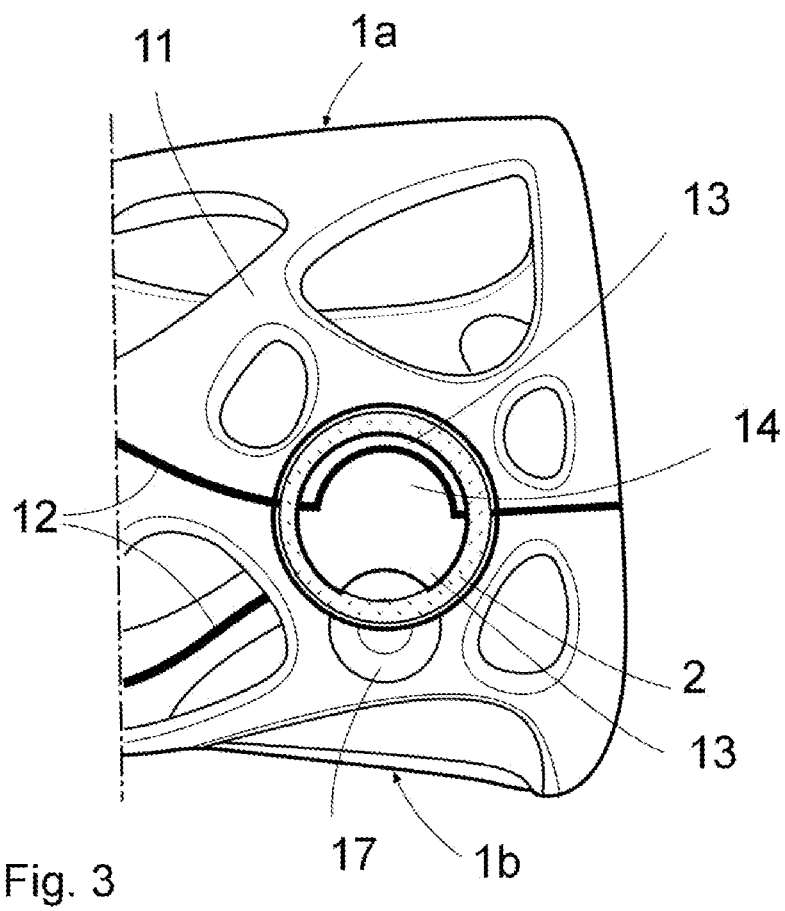
FIG. 3 portrays an elevational view of a distal portion of the device in FIG. 1, wherein the attachment, by means of one of the elastic O-rings, of the two parts constituting the same may be seen.

The parts (1a, 1b) comprise a number of fasteners featuring raised portions (13) for the coupling of elastic O-rings (2) which clamp said parts in the normal-use position, as may be observed in the detail of FIG. 3.

As has been stated, the elastic O-rings (2) responsible for providing rigidity to the assembly, and for immobilising the parts (1a, 1b) may feature different elastic densities in order to establish a strong coupling between the parts (1a, 1b), or enable a certain separation between the same in the event of inflammation of the immobilised limb.

The use of elastic O-rings of lower elastic density (Shore 40) enables the separation of the parts (FIGS. 5a and 5b), enlarging the compartment.

Figure 1:
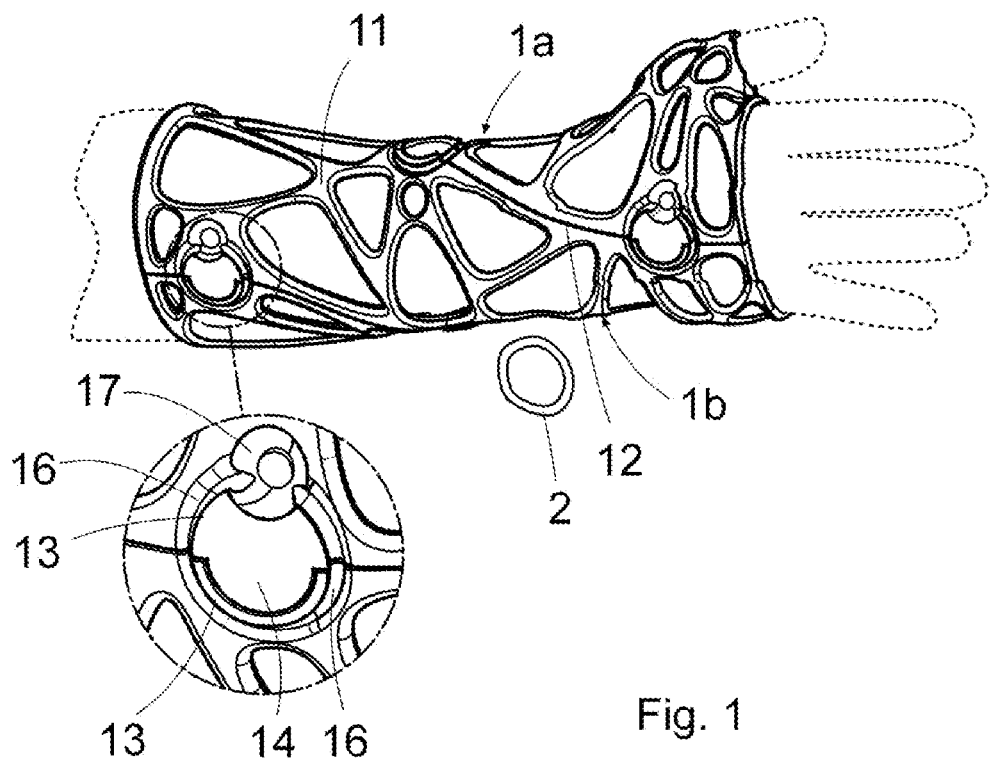
FIG. 1 portrays a perspective view of an example of an embodiment of the post-traumatic immobilisation device in accordance with the invention, and an enlarged detail of the area for the coupling of one of the elastic O-rings for the closure thereof.
Figure 2:
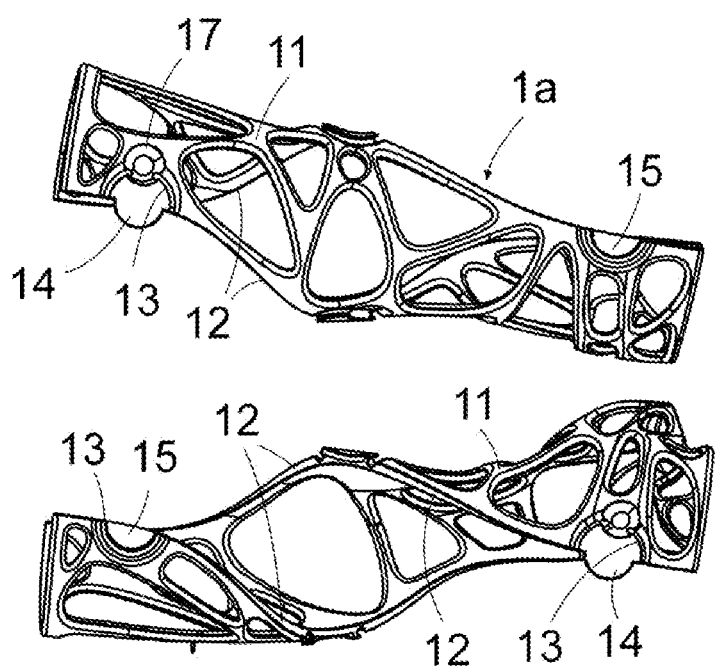
FIG. 2 portrays a perspective view of the two parts of the device in the previous figure, separated and revealing the helicoidal shape of the same.
Figure 4:
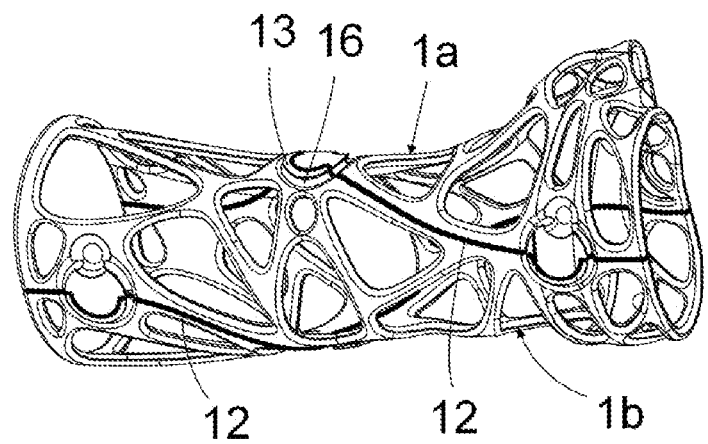
FIG. 4 portrays an upper perspective view of the device in FIG. 1 wherein the curved connecting ends of the two parts are highlighted in order to facilitate the appreciation of the helicoidal shape of the same.

In FIG. 4, the device in FIG. 1 is portrayed in a rotated position, highlighting the curved ends (12), in this case helicoidal ends, of the parts (1a, 1b) intended to face each other and to be coupled together by means of the elastic O-rings of the fasteners.

Figure 5A:
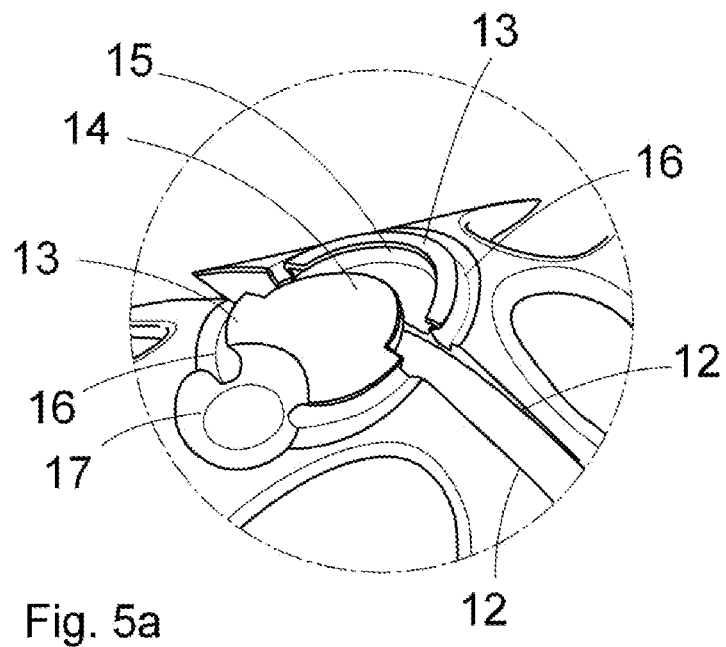
FIG. 5a portrays a detail in perspective of one of the clips, featuring raised portions defined at the facing ends of the parts for the coupling of clamping elastic O-rings; said parts are portrayed slightly apart, and in this case featuring the channel for the coupling of the elastic O-ring and a spherical recess for the grasping and release of said elastic O-ring.
Figure 5B:
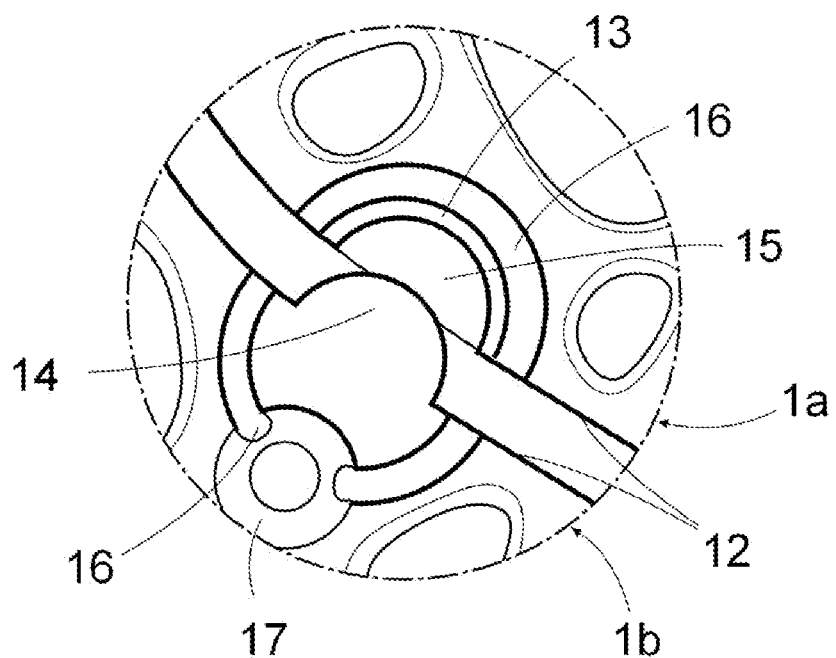
FIG. 5b portrays an elevational detail of the same detail as that of FIG. 5a, with the two parts in the coupled position and the elastic O-ring in the assembled position.

In the detail in perspective portrayed in FIG. 5a, the parts (1a, 1b) feature in correspondence with their fasteners a number of tabs (14) and a number of complementary seats (15) for their coupling in the normal-use position.

These tabs (14) enable the positioning and orientation of the two parts of the device, facilitating the subsequent placing of the O-rings.

The raised portions (13) defined on the parts (1a, 1b) for the coupling of the elastic O-rings (2) are delimited by a number of channels (16) defined on the external surface of said parts, open at the curved connecting ends (12) of the same; said channels featuring dimensions suited for the lodging within the same of the corresponding elastic O-ring (2).

In the example of an embodiment portrayed in FIGS. 1 to 5b, the parts (1a, 1b) feature at a peripheral point of the channels (16) a recess (17) of a width greater than that of the former, in this case of a spherical shape, forming an area for the grasping and removal of the corresponding elastic O-ring.

These recesses (17) facilitate the opening of the fasteners by means of the removal of the elastic O-ring.

Figure 6:
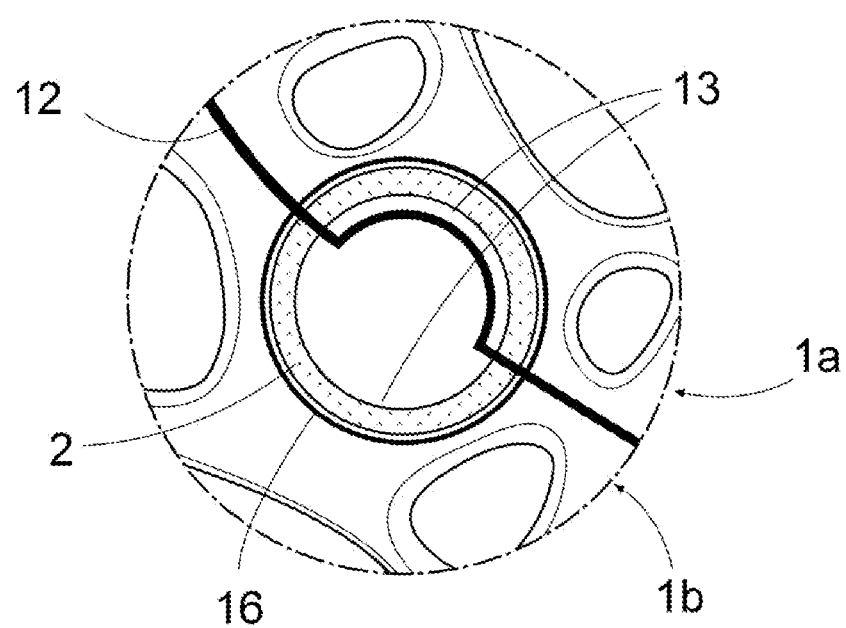
FIG. 6 portrays an elevational detail of a variant of the embodiment of one of the clips, wherein the channel for the housing of the elastic O-ring lacks the spherical recess for the grasping and removal thereof, providing a fixed coupling.

In the variant of the embodiment portrayed in FIG. 6, the channels (16) lack the aforementioned recess (17) in such a way that the corresponding elastic O-ring (2) is lodged within the channel (16), preventing its grasping and removal, in this case providing a fixed coupling.

Thus, the recess (17) endows the fastener with a "removable" nature, enabling easy access and removal of the O-ring, or a "fixed" nature, as portrayed in FIG. 6, preventing access by the user to the O-ring, which remains fixed throughout the immobilisation.

In an embodiment of the invention, the parts (1a, 1b) are obtained by means of 3D printing with a P/PA 2200 biocompatible material with zero porosity. In this particular case, the parts are architecturally produced with an EOSINT P760 printer with SLS technology following the ISO 10993-1 standard.

It should be mentioned that the mesh (11) may present different structures (greater or smaller mesh size), according to the area required, endowing the affected limb with greater comfort and conditioning.

At the time of processing, it is possible to include an access window in the structure of the parts (1a, 1b) for the application of dressings (postoperative incisions) without affecting the structure, rigidity, torsion or proportion of the parts.

In a preferred embodiment of the invention, the procedure for the manufacture of the device described above by means of 3D printing techniques comprises: a) a protocol for obtaining anthropometric data; b) the adaptation of post-traumatic immobilisations by means of a computer-assisted system; and c) the delivery to the user of a file with the result, for viewing and subsequent submission to 3D printing equipment.

The protocol for the obtaining of data comprises:
Entering the patient's general data into a computer application, and optionally supplementary data to constitute the final result of the immobilisation (Select limb or affected area; upper extremities [fingers, wrist, forearm, arm, shoulder] or lower extremities [foot, leg, thigh]).

Scanning the affected part with scanner-specific software.
In the event that the affected limb to be scanned to obtain data cannot be moved for various reasons, or because it is covered by a compression bandage or plaster, there exists the possibility to obtain the volumetric data of the opposite limb, and to perform an automatic "mirror" calculation. In this way, in 90% of cases, the data obtained are the same as those of the limb which cannot be scanned. In the remaining 10% of cases, the medical specialist will reject this technique due to the existence of malformations and/or clearly different volumes (sportspersons).

The automatic generation by the computer application of a 3D virtual model of the immobilisation device and the on-screen viewing of said 3D virtual model.

The selection on the 3D model, part by part, of the various characteristics, such as the position of the terminals for the electro-stimulation of the affected limb, the position of openings (windows for dressings) on the affected limb, the system for fastening with elastic O-rings, be it "fixed" or "removable", or the final colour of the immobilisation device, to be selected from a predetermined colour card.

For the computer system to be able to adapt the immobilisation device to the patient, it must know the exact position of the injured limb in the three-dimensional space of the anthropometric data acquired.

To this end, the system features a specific application for a portable three-dimensional scanner, in this case the "STRUCTURE" scanner (https://store.structure.io/store).

This application comprises:
Simple, rapid scanning of the affected part of the patient.
Establishing the position of the injured limb by means of tools which will guide the user in obtaining data.
Scanning under adverse lighting conditions.
The automatic elimination of unnecessary areas obtained by the scanner.
The system performs the following operations by means of its hardware:
The correct position to be adopted by the patient will be displayed on the screen of the system.
The virtual projection on screen of the profile of a limb to be scanned, which the user should fit, both horizontally and vertically, over the patient's limb.
The projection of control points within the profile, which aid the user in positioning at the correct distance to commence the sweep for data acquisition.
When the application detects that the scanner has been correctly positioned, data acquisition will begin automatically.

This method enables all the acquisitions to start at the same initial position, revealing the exact (three-dimensional) position of the patient's limb by means of the data acquired. It also enables the determination of the volume of the patient's limb and automatically facilitates the delimitation of the affected area and the elimination of any unnecessary "geometry".

This process saves costly transfer, rotation, volume and other calculations.

On completion of the sweep with the scanner, the result will be seen on screen, and the specialist physician will use control keys to delimit the distal and proximal ends (windows) where the software will begin generating the mesh, and the system will proceed to perform the automatic adaptation of the post-traumatic immobilisation device.

For the construction of the immobilisation device, an application is used that ensures the receipt of instructions via scripts in "Python" language, without human intervention, ensuring the automation of the aforementioned processes.

The script with the instructions includes the following tasks for execution:

Positioning of the mesh on the patient's limb

Figure 7:
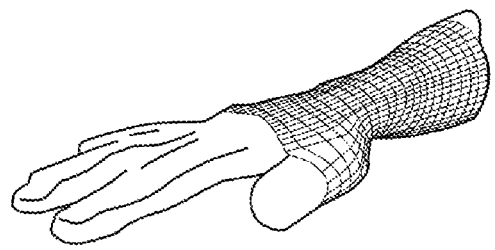
FIGS. 7, 8, 9, 10a, 10b, 11, 12a and 12b portray successive stages of the automatic adaptation of the post-traumatic immobilisation device during the manufacture of the device in the preceding figures, in accordance with the procedure of the invention.
Figure 8:
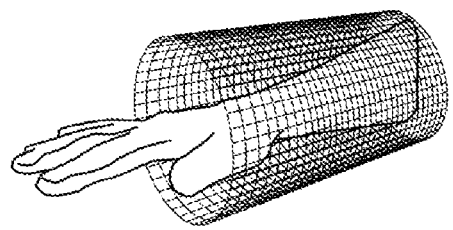

Adjustment of the mesh (FIG. 7, FIG. 8)

Figure 9:
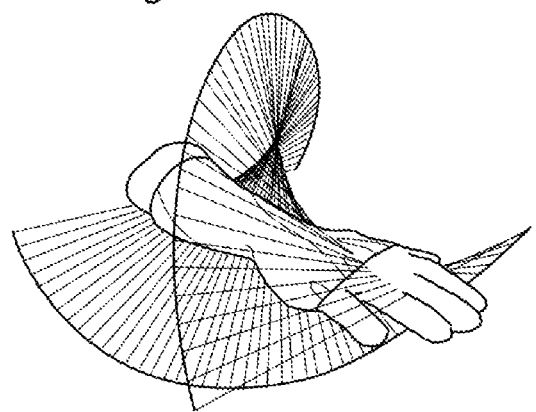

Positioning of the longitudinal, helicoidal separation (variable torsion) (FIG. 9)

Figure 10A:
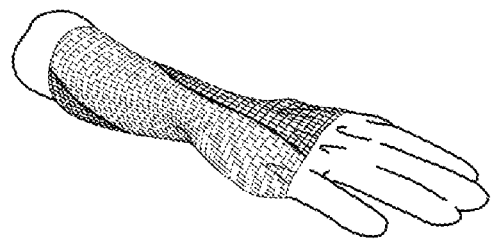
Figure 10B:
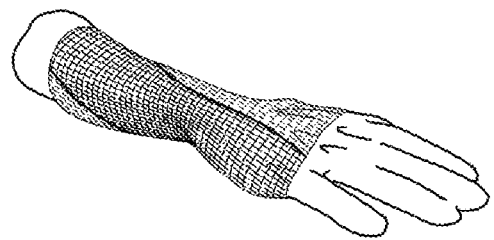

Division into two parts (FIG. 10)

Perforation pattern (Voronoi diagram pattern)

Figure 11:
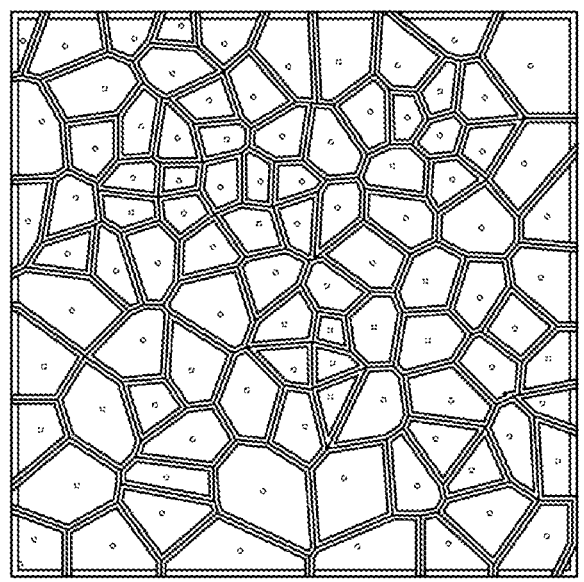

Adjustment of the correct method (greater or smaller mesh) to the pattern (FIG. 11)

Figure 12A:
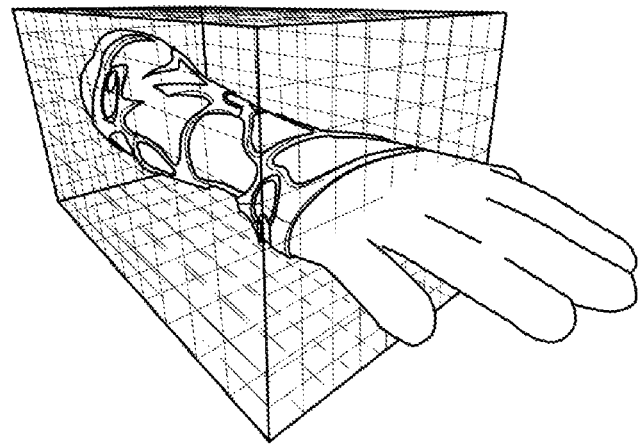
Figure 12B:
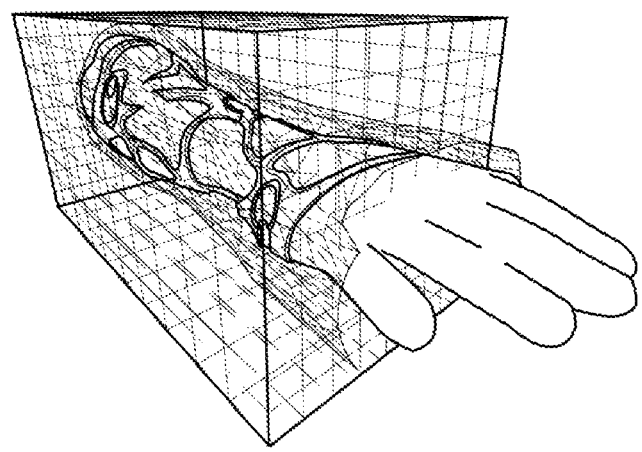

Application of the thickness of the parts (according to desired immobilisation) (FIG. 12)

Fixing of the housings for the O-rings

Fixing of the linking tabs (FIG. 12)

On completion of the construction process, the file with the result is returned to the user for viewing and subsequent sending to 3D printing equipment.

The nature of the invention having been sufficiently described, likewise an example of a preferred embodiment, it is stated for all appropriate purposes that the materials, shape, size and disposition of the elements described may be modified, provided that this shall not entail a variation in the essential characteristics of the invention claimed below.

The invention claimed is:

1. A post-traumatic immobilisation device, having an architectural form using biocompatible material with a rounded shape, comprising:
    at least two complementary rigid parts in form of a mesh, defining respective concave cavities and
    comprising: a plurality of fasteners having raised portions for coupling of a plurality of elastic O-rings which clamp the rigid parts to one another in a normal-use position,
    wherein said rigid parts delimit a housing for the adjusted holding of the part of the body to be immobilized;
    wherein the rigid parts feature heliocoidal curved connecting ends which determine a single coupling position of said rigid parts and feature at curved connecting ends a plurality of tabs and a plurality of complementary seats for centering and orientation of the rigid parts in a normal-use position; and
    the raised portions for clamping of the elastic O-rings are delimited by a plurality of channels defined on an external surface of the rigid parts, open at the curved connecting ends of said rigid parts, and have dimensions for lodging within the channels of a corresponding elastic O-ring.

2. The post-traumatic immobilisation device as claimed in claim 1, comprising interchangeable elastic O-rings of different elastic densities to immobilise the rigid parts in a normal-use position, or to enable a separation between said rigid parts, increasing dimensions of the housing to hold the immobilised body part in the event of inflammatory processes of the immobilised part.

3. The post-traumatic immobilization device as claimed in claim 1 wherein the rigid parts at a peripheral point of the channels a recess forming an area for the grasping and removal of the corresponding elastic O-ring.

4. A method for the of manufacture of the device of claim 1,
    comprising:
        a) a protocol for obtaining data which comprises:
            entering a patient's general data into a computer application, and supplementary data to constitute a final result of the immobilisation device, selecting a limb or affected part of the upper or lower extremities;
            scanning the affected part with scanner-specific software;
            automatic generation by the computer application of a 3D virtual model of the immobilisation device and on-screen viewing of said 3D virtual model;
            selecting on the 3D model, part by part, of characteristics including position of terminals for electro-stimulation of the affected limb, position of openings on the affected limb, the system for fastening with elastic O-rings, by fixed or removable coupling or a final colour of the immobilisation device;
        b) the step-by-step adapting and constructing of the rigid parts of the post-traumatic immobilisation device by an application which receives instructions via scripts, without human intervention, and which executes following tasks:
            positioning of the mesh on the patient's limb;
            adjustment of the mesh;
            positioning of longitudinal, helicoidal separation;
            division into two parts;
            perforation pattern;
            adjustment of a correct method (using greater or smaller) mesh to the pattern;
            application of a thickness of the parts;
            fixing of the housings for the O-rings;
            fixing of the linking tabs;
        c) returning a file with the result to a user for viewing and subsequent sending to a 3D printer.

* * * * *